(12) United States Patent
Woloszko et al.

(10) Patent No.: US 7,248,930 B1
(45) Date of Patent: Jul. 24, 2007

(54) MEDICAL ELECTRICAL LEAD

(75) Inventors: Jean Woloszko, San Diego, CA (US); Antoine Camps, Rye (NL); Ron Van der Kruk, Bunde (NL)

(73) Assignee: MedTronic, Inc., Minneapolis, MN (US)

( * ) Notice: Subject to any disclaimer, the term of this patent is extended or adjusted under 35 U.S.C. 154(b) by 0 days.

(21) Appl. No.: 09/514,906

(22) Filed: Feb. 28, 2000

Related U.S. Application Data (62) Division of application No. 08/820,473, filed on Mar. 17, 1997, now Pat. No. 5,938,596.

(51) Int. Cl.
*A61N 1/05* (2006.01)
(52) U.S. Cl. .................. 607/118; 600/377; 600/393
(58) Field of Classification Search .......... 600/377, 600/393, 509, 374; 607/115–118, 126, 130, 607/132
See application file for complete search history.

(56) References Cited

U.S. PATENT DOCUMENTS

| | | | |
|---|---|---|---|
| 3,654,933 A | | 4/1972 | Hagfors ............... 128/418 |
| 4,276,882 A | * | 7/1981 | Dickhudt et al. ........... 607/116 |
| 4,979,511 A | * | 12/1990 | Terry, Jr. ................. 600/377 |
| 5,344,438 A | | 9/1994 | Testerman et al. ......... 607/118 |
| 5,699,796 A | * | 12/1997 | Littmann et al. .......... 600/374 |

* cited by examiner

*Primary Examiner*—Lee S. Cohen (57) ABSTRACT

A medical electrical lead for establishing an electrical connection with a tissue of the body, the lead having a lead body and a semi-cylindrical cuff. In the preferred embodiment the semi-cylindrical cuff features one or more electrodes. The semi-cylindrical cuff having a long flap which wraps about the cuff and a short flap which wraps about the long flap. The semi-cylindrical cuff is relatively stiff as compared to the short flap. The short flap, in turn, is relatively the same stiffness as the long flap. The stiffness of each flap may be varied, however, so that one is more or less than the other, and in turn, than the cuff. Through such a multi-flap construction the electrodes may be positioned proximal to a nerve in such a manner that the mechanically induced damage may be minimized or even entirely eliminated. Finally, a method of implanting such an electrode is also disclosed.

5 Claims, 11 Drawing Sheets

MEDICAL ELECTRICAL LEAD

This application is a division of U.S. patent application Ser. No. 08/820,473 filed Mar. 17, 1997, now U.S. Pat. No. 5,938,596, for "Medical Electrical Lead" to Woloszko et al.

FIELD OF THE INVENTION

This invention relates to the field of body-implantable medical device systems, and in particular to a medical electrical lead which features a semi-cylindrical cuff designed to stimulate or sense or both nerve tissue.

BACKGROUND OF THE INVENTION

Modern electrical therapeutic and diagnostic devices, such as pacemakers or nerve stimulators for example, require a reliable electrical connection between the device and the body. In cases of nerve stimulators, in particular, chronically reliable electrical connections have been difficult to attain. In a chronic setting it has been found many medical electrical leads may damage a nerve either mechanically or electrically or both.

Mechanically induced damage includes thickened epineurium due to accumulation of connective tissue between the electrode and the nerve, increased subperineural and endoneural connective tissue, endoneural edema, demyelinization, axonal degeneration and frank axonal loss. Such damage may be caused in several ways. First, if the lead and in particular the electrode which interfaces with the nerve does not move with the nerve, then abrasion may result. Second, the presence of the lead and in particular the electrode, a foreign object, may cause edema or swelling of the nerve. As the nerve swells it may be constricted by the lead. A compressive force may thereby be induced upon the nerve. In the past a so-called "self-sizing" nerve electrode was fashioned to avoid such damage. Such an electrode may be seen in the U.S. Pat. No. 4,920,979 to Bullara entitled "Bidirectional Helical Electrode for Nerve Stimulation and assigned to the Huntington Medical Research Institute. To date, however, such electrodes have not been wholly satisfactory. Electrically induced damage may also be caused by a chronic nerve electrode. Such damage results in, among other injuries, axonal degeneration as well as nerve edema. While it has been shown that the type of electrical stimulation, e.g. frequency, waveform, amplitude, may be a significant factor, the actual electrode design may also affect the degree of electrically induced damage. In particular a medical lead which provides the optimal electrical characteristics for the desired therapy is needed.

SUMMARY OF THE INVENTION

The present invention provides a medical electrical lead for establishing an electrical connection with a tissue of the body. The present invention is particularly suited for use as a nerve electrode and essentially comprises a lead body and a semi-cylindrical cuff. In the preferred embodiment the semi-cylindrical cuff features one or more electrodes. The semi-cylindrical cuff having a long flap which wraps about the cuff and a short flap which wraps about the long flap. The semi-cylindrical cuff is relatively stiff as compared to the short flap. The short flap, in turn, is relatively the same stiffness of each flap. The stiffness of each flap may be varied, however, so that one is more or less than the other, and in turn, than the cuff. Through such a multi-flap construction the electrodes may be positioned proximal to a nerve in such a manner that the mechanically induced damage may be minimized or even entirely eliminated. Finally, a method of implanting such an electrode is also disclosed.

BRIEF DESCRIPTION OF THE DRAWINGS

The present invention may be better understood and appreciated with reference to a detailed description of a specific embodiment of the invention, when read in conjunction with the accompanying drawings.

FIGS. 17 A, B, and C depict alternative embodiments of the medical electrical lead.

FIGS. 18 A and B depict alternative embodiments of the electrodes used in the medical electrical lead.

DETAILED DESCRIPTION OF THE DRAWINGS

Figure 1:
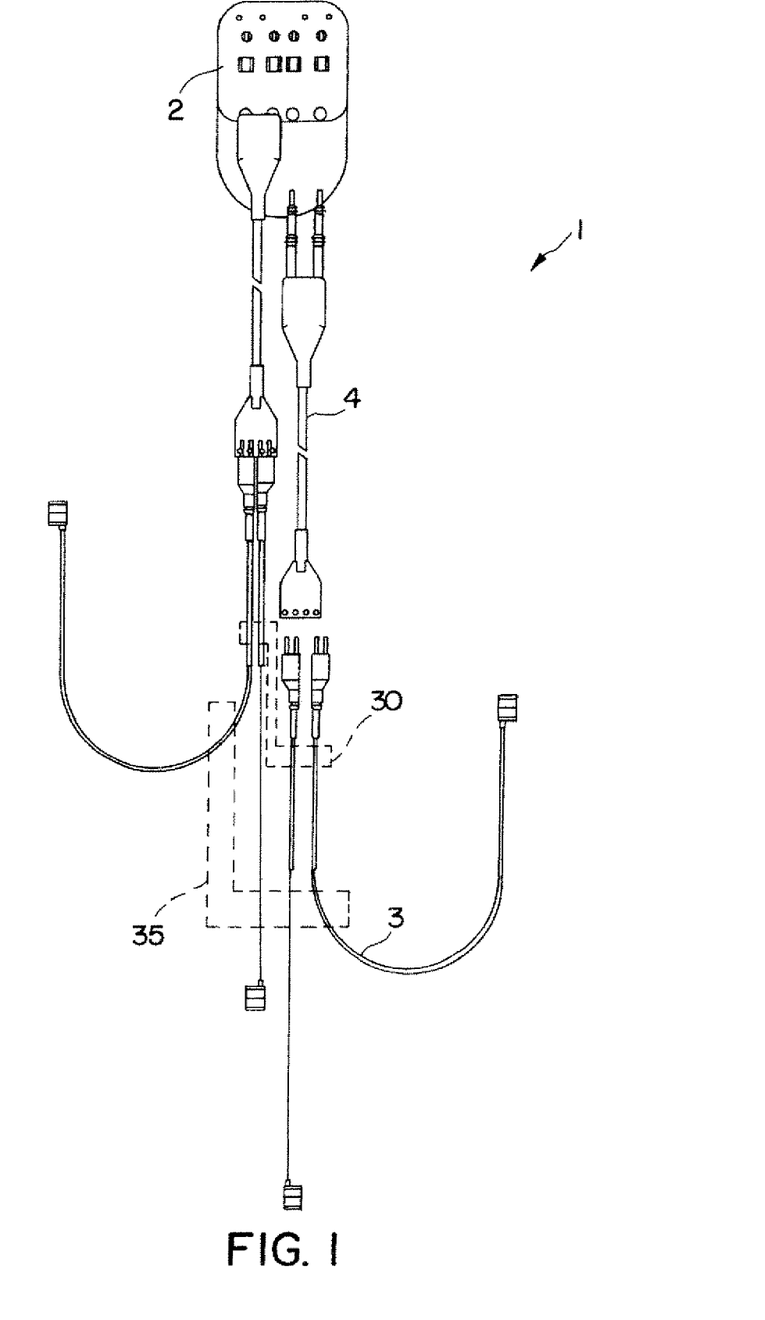
FIG. 1 depicts a system for nerve stimulation featuring several medical electrical leads.

FIG. 1 shows a system 1 for nerve stimulation which uses several medical electrical leads of the present invention. As seen, the system features the implantable pulse generator 2 electrically coupled to one or more medical electrical leads 3 by extension cables 4. In the preferred embodiment the pulse generator is the preferred Medtronic model 3025 Sacral Root Stimulator. This device is particularly designed for stimulation of the nerves of the sacral root, although other types of stimulators may also be used. The lead extensions are the Medtronic model 3091 extension cables, although other such devices may also be used. As seen, the system of the preferred embodiment features four medical electrical leads coupled to the implantable pulse generator. The system further preferably features an anchoring sleeve and stabilizing block to maintain the leads in position. These are illustrated below in FIG. 2A.

Figure 2A:
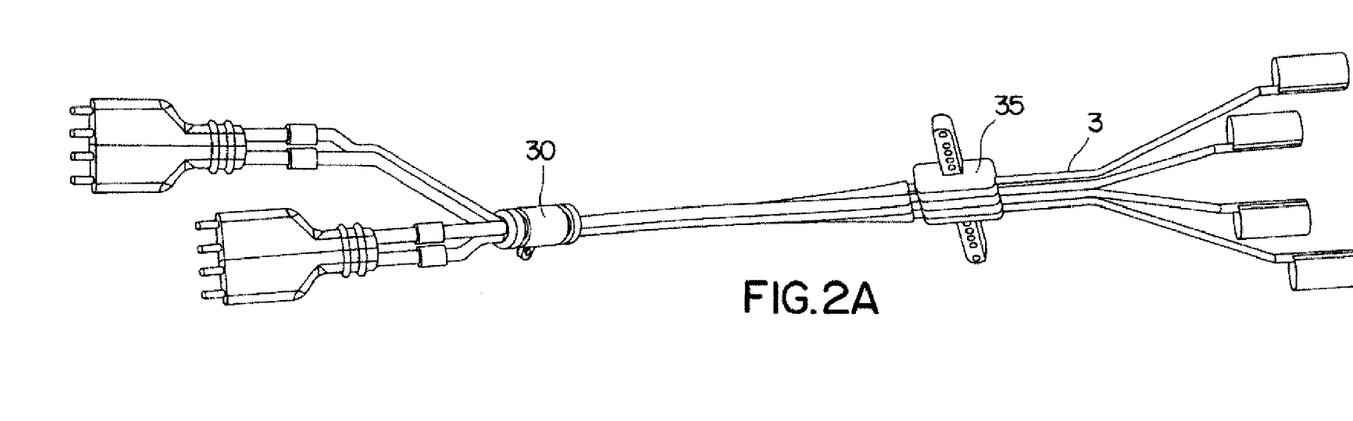
FIG. 2A is a view of the four leads used in the system of FIG. 1 and the anchoring sleeve and anchoring block which secure the leads.

FIG. 2A is a view of the four leads used in the system of FIG. 1 and the anchoring sleeve and anchoring block which are used to secure the leads. As seen, anchoring sleeve 30 is positioned along the larger diameter section of each lead body of the lead. Positioned distal to the anchoring block is the stabilizing block 35. As seen, stabilizing block is positioned along the thinner diameter section of the lead bodies of the leads. As discussed below, the suture sleeve functions to secure the leads from moving longitudinally relative to one another once they are implanted. Suture sleeve is fastened to the surrounding tissue as is well known. Stabilizing block functions to stabilize each of the distal sections of the leads in position once they are implanted so that implantation of additional leads and the positioning of their electrodes about a nerve will not disturb those leads and electrodes already positioned.

Figure 2B:
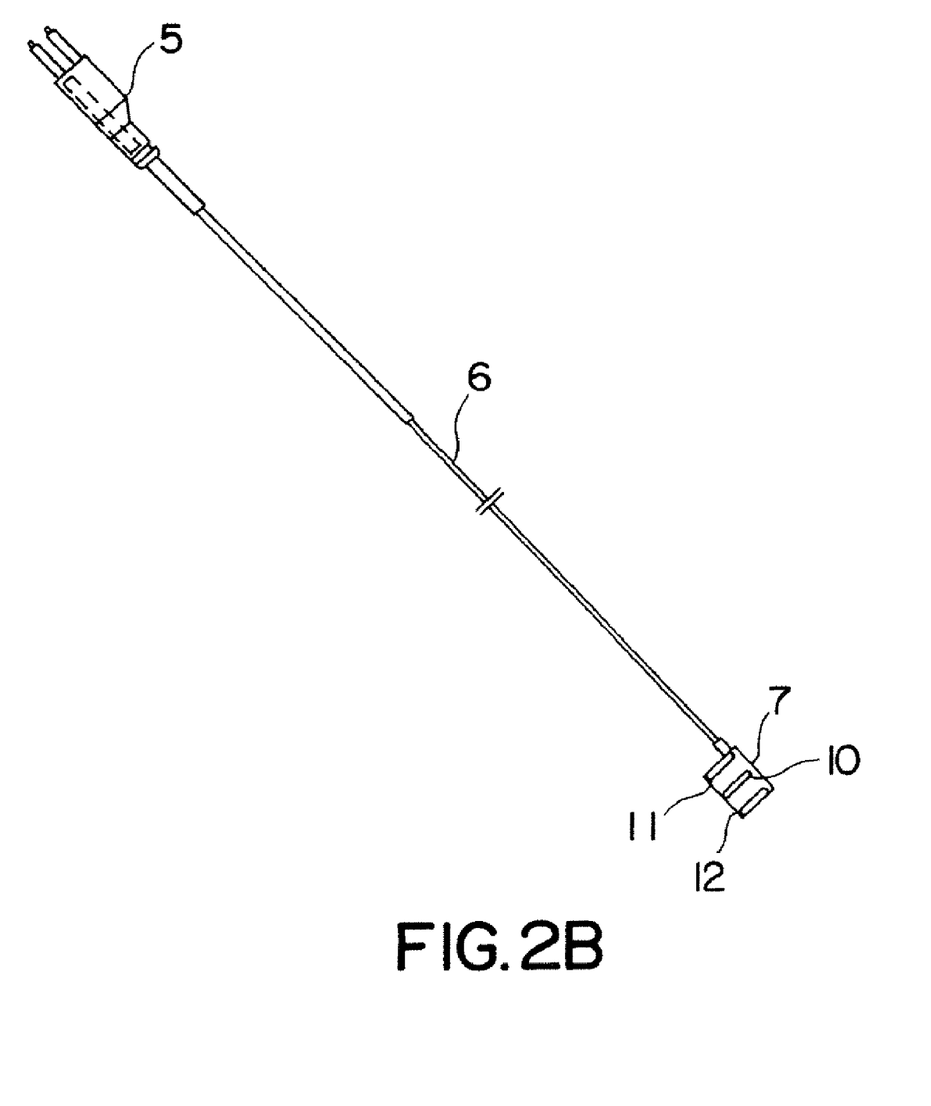
FIG. 2B is a perspective view of the medical electrical lead.

FIG. 2B is a detailed view of a single medical electrical lead 3 according to the present invention. As seen, the lead has essentially three portions, the connector portion 5, the lead body 6, and an electrode portion 7. The connector portion in the preferred embodiment features two pins each of which are electrically coupled to a separate conductor in the lead body. The lead body 6 is preferably constructed of three bundle stranded wire conductors each of which is insulated from the other. The insulation is PTFE, although other types of insulations may also be used, such as silicone.

Positioned at the distal end of the lead body is the electrode portion 7. In the preferred embodiment the electrode portion features three tab electrodes, the inner electrode tab 10 being electrically coupled to a first conductor and the outer two tab electrode tabs 11, 12 electrically coupled to the second conductor of the lead body. In the preferred embodiment the outer two electrode tabs 11, 12 are coupled as anodes while the inner electrode tab 10 is coupled as a cathode. Through this configuration a guarded bipolar electrode is presented to the nerve. A guarded bipolar electrode is preferred because it confines the stimulating current within the electrode cuff and thereby minimizes the undesired spread of current to the surrounding tissues.

Figure 3:
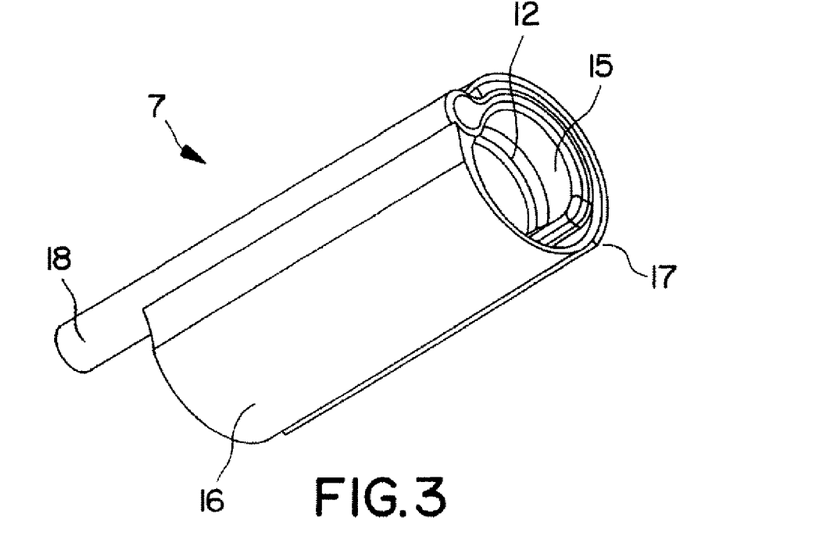
FIG. 3 is a detailed view of the electrode portion of the medical electrical lead.

FIG. 3 is a detailed perspective view of the electrode portion. As seen the electrode portion 7 is constructed from three elements. Semi-cylindrical cuff 15 which has an inner long flap 16 mounted to root portion 18 of cuff so as to extend about the opening of the semi-cylindrical cuff. Due to the orientation of the long flap relative to the semi-cylindrical cuff, the lumen is defined. Enveloping the outer end portion of the long flap, is an outer short flap 17. Through this configuration the self-sizing cuff is formed which permits the cuff to stay mounted around the nerve and not be dislodged through the swelling of the nerve. Positioned within the interior surface of the semi-cylindrical cuff are three tab electrodes (only one of which is seen as 12.)

Figure 4A:
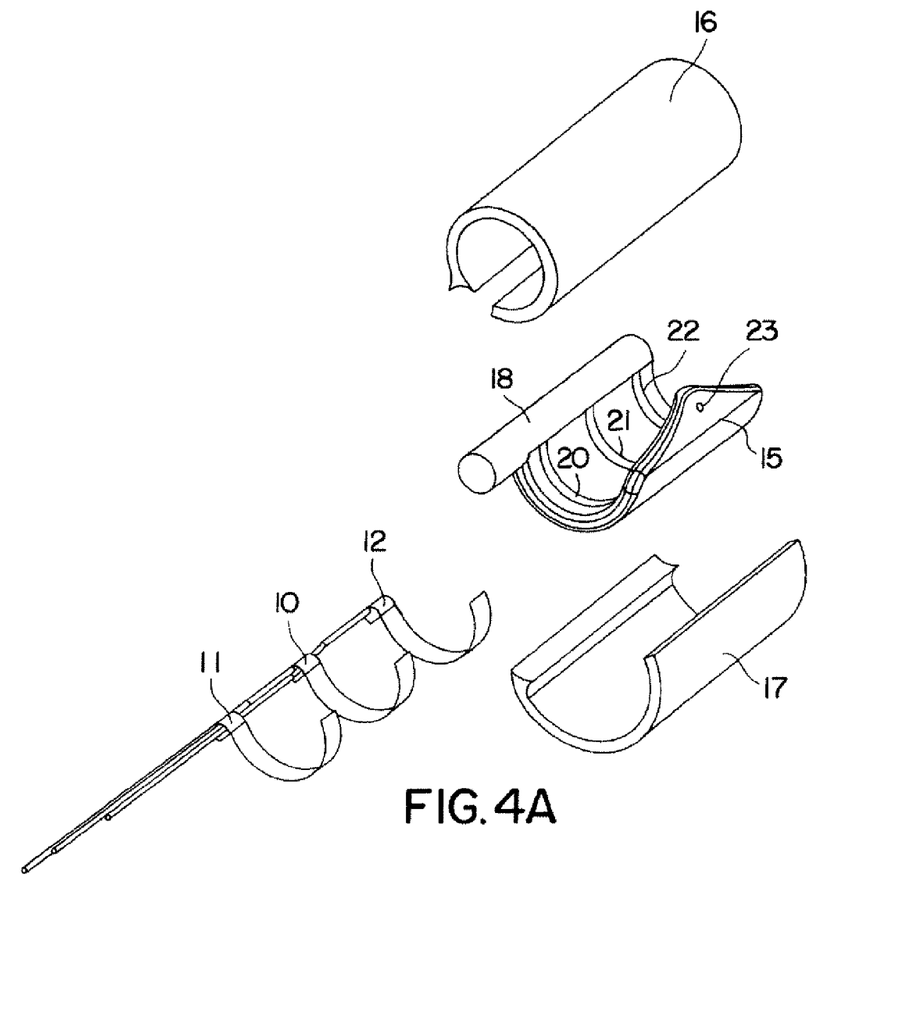
FIG. 4A is an exploded view of the electrode portion shown in FIG. 3.

FIG. 4A is an exploded view of the electrode portion. As seen, the electrode portion features a semi-cylindrical cuff. The semi-cylindrical cuff has three cylindrical grooves 20–22 on the inner surface. Three tab electrodes 10–12 are positioned in the grooves. The tab electrodes are preferably constructed from a platinum-iridium alloy, although other materials may also be used such as a conductive polymer. Extending in the opposite radial direction of the semi-cylindrical cuff 15 is the long flap 16. The long flap has a cylindrical design. Extending in the same direction of the semi-cylindrical cuff (and thus opposite radial direction of the long flap) is the short flap 17. The short flap also has a cylindrical shape. In the preferred embodiment the semi-cylindrical cuff is relatively stiff as compared to the short flap. The short flap, in turn, is relatively more stiff than the long flap. Of course, the relative stiffness of the flaps in the cuff may be different. Located at the radial distal end of the semi-cylindrical cuff is a suture hole 23 which may be used to manipulate the cuff during the implant process, described below.

Figure 4B:
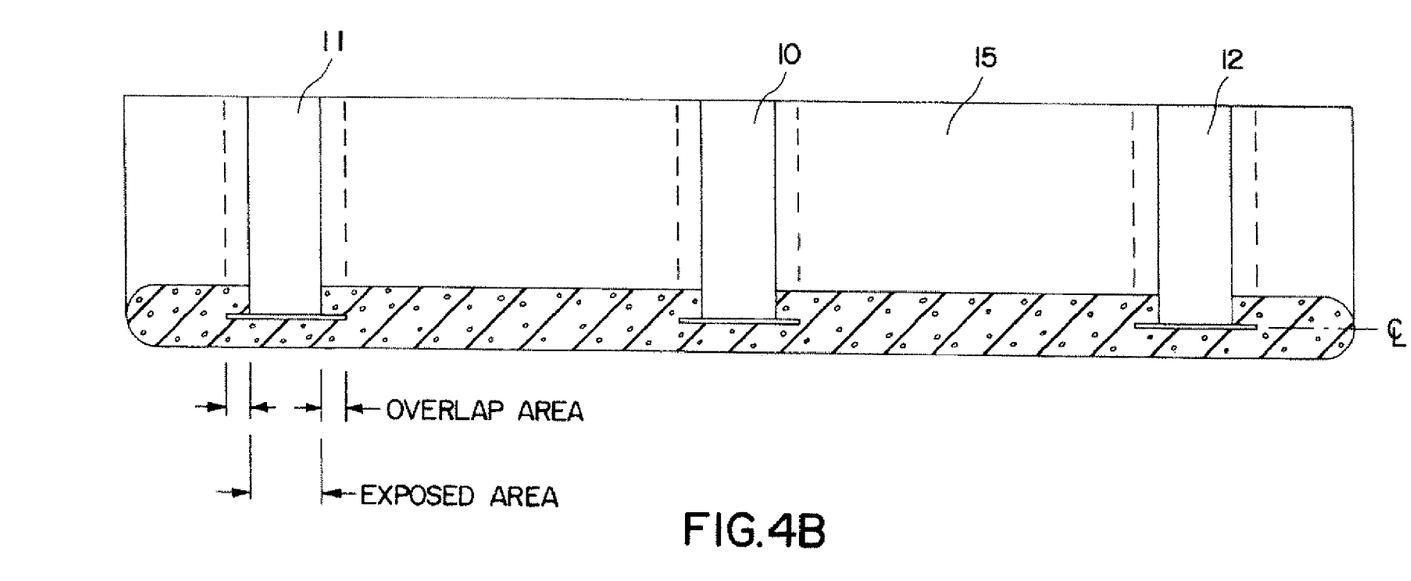
FIG. 4B is a sectional view of the electrode portion showing the placement of electrode tabs within the semi-cylindrical cuff.

FIG. 4B is a longitudinal cross-section of semi-cylindrical cuff. As seen, electrode tabs 10, 11 and 12 are positioned within cuff recesses in the cuff. Recesses are dimensioned such that there is an overlap of material along the edges of each electrode tab. Through this overlap the electrode tab is mechanically secured within the cuff. In the preferred embodiment overlap area is 0.2 inches in length on each side and the exposed area is 0.6 inches in length. Each electrode tab is positioned in the recess to a depth corresponding to the center of the cuff thickness.

Figure 5:
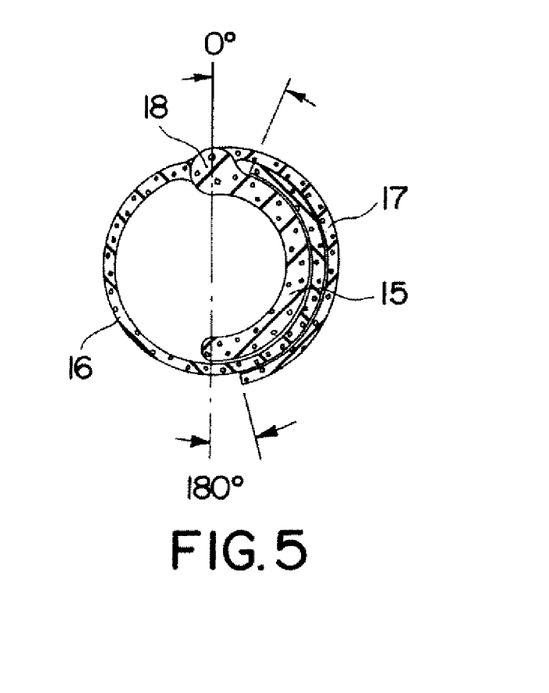
FIG. 5 is a sectional view of the electrode portion showing the various radial positions of the semi-cylindrical cuff, long flap and short flap.

FIG. 5 shows the relative radial orientations of the flaps and the semi-cylindrical cuff. As seen, the semi-cylindrical cuff 15 extends for approximately 180°, although other radial lengths may also be used, including from 270° to 90°. Moreover, although depicted in the figures as a cylindrical design, this cuff may also have other designs, such as square or octagonal, for example, and may also be of other designs entirely, such as helical. The long flap 16 preferably extends in a radial direction opposite of the semi-cylindrical cuff for an amount of 340°, although other radial lengths may also be used, such as between 360°–180°. The short flap 17, in turn, extends in the same radial direction as the semi-cylindrical cuff and preferably extends for a radial distance of 120°, although other radial distances may also be used, including anywhere between 45°–360°. Through this construction, the relative radial directions and distances of the semi-cylindrical cuff and the flaps, as well as through various stiffnesses, the self-sizing property of the electrode portion is provided. Self-sizing property is an essential aspect of the present invention because it permits the electrode to accommodate swelling of the nerve without damaging the nerve while maintaining electrical contact. Moreover, partial dislodgment due to pulling or movement of the electrode portion from the nerve is automatically controlled through the elastic property of the flaps, i.e. the electrode re-seats itself back onto the nerve it has partially dislodged.

Figure 6:
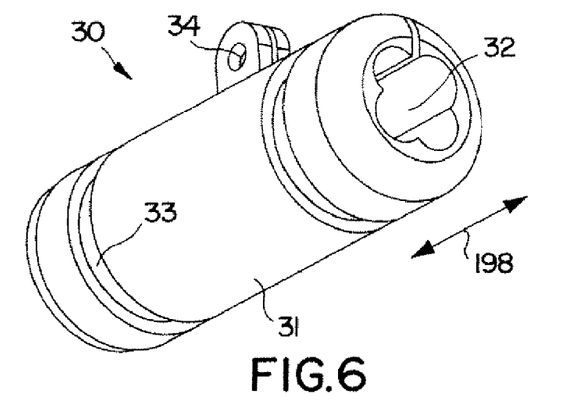
FIG. 6 is an anchoring sleeve used on the medical electrical lead.

FIG. 6 is the suture sleeve used in the system of FIG. 1 and clearly shown in FIG. 2A. As seen, the suture sleeve 30 has a body 31 having a lumen 32 therethrough. The lumen is shaped to accommodate four cylindrical lead bodies therein although less lead bodies can also be positioned therein. The suture grooves 33 on the body permit the body to be cinched or tied to the lead bodies. The suture hole 34 permits the body to be sutured to the surrounding tissue. The suture sleeve functions to secure the leads from moving longitudinally as indicated by arrow 198.

Figure 7:
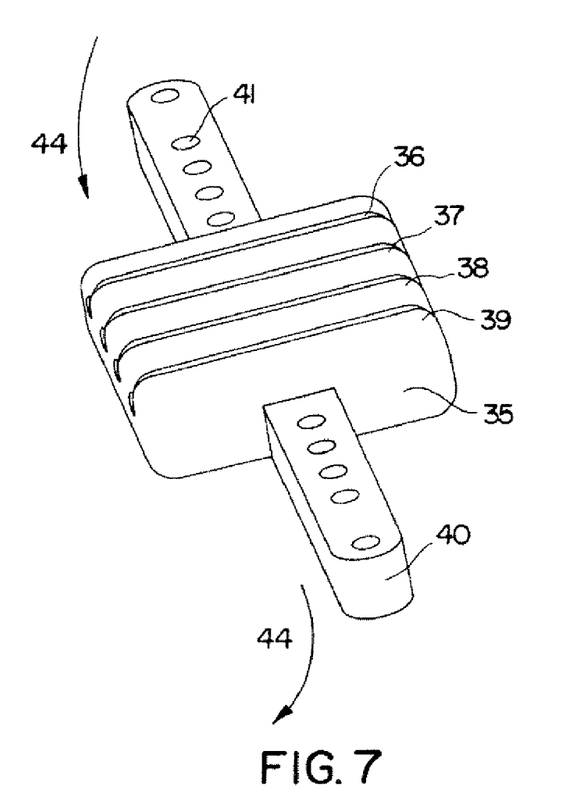
FIG. 7 is an anchoring block used on the medical electrical lead.
Figure 8:
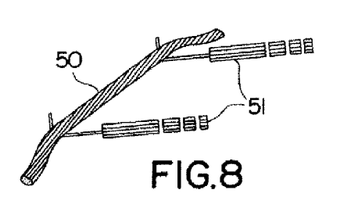
FIGS. 8–16 depict the method of implanting the medical electrical lead around the nerve.

FIG. 7 depicts the stabilizing block used in the system of FIG. 1 and clearly shown in FIG. 2A. The stabilizing block 35 preferably has four slots 36–39 to accommodate four lead bodies. Slots are accessed by the four leads by bending block in direction 44. Slots are dimensioned in their bottom to correspond to and frictionally engage with lead body although they may also have other shapes, e.g. rectangular. Tabs 40 extend from the block to permit the block to be sutured into the surrounding tissue using holes 41. Stabilizing block stabilizes each of the electrode portions 7 of each lead from moving out of position while the outer leads are implanted.

Figure 9:
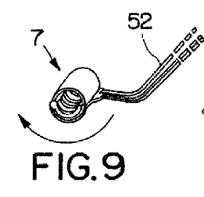
Figure 10:
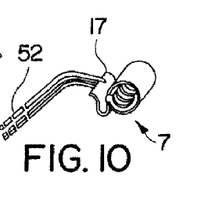
Figure 11:
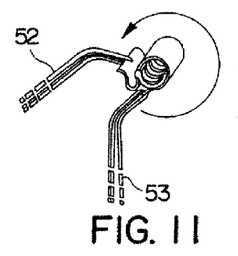
Figure 12:
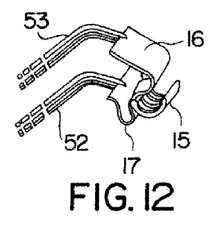

FIGS. 8–16 depict the method of implanting the present invention. As seen in FIG. 1, the nerve 50 is surgically exposed and elevated from its position using two nerve hooks 51. As seen in FIGS. 9 and 10 forceps 52 are used to gently pull the short flap 17 from its biased position while holding the electrode portion 7 by the lead body. Next, using another pair of forceps 53 the long flap 16 is gently removed from its biased position so the opening of the half cuff 15 is exposed.

Figure 13:
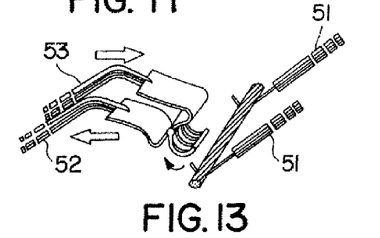
Figure 14:
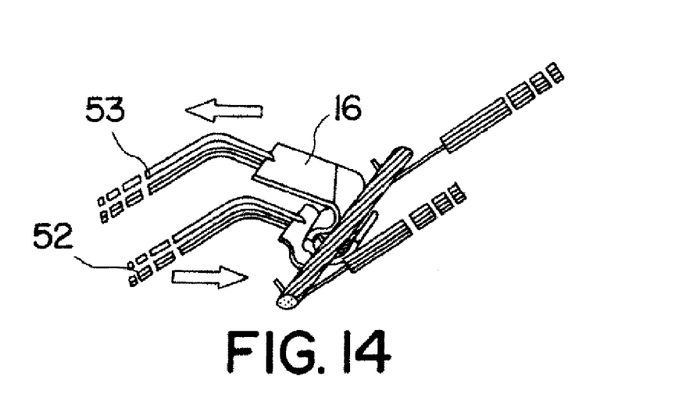
Figure 15:
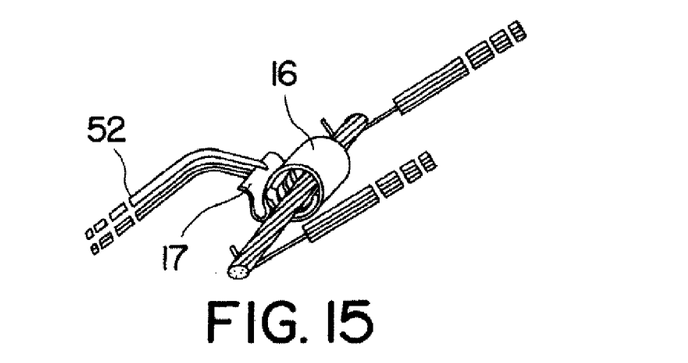

Turning to FIG. 13, using the two forceps, 52, 53 the two flaps 16, 17 are moved in opposite linear directions in order to incline the half cuff and present the tab electrodes for contact to the nerve. This is depicted in FIG. 14. Once correctly positioned, the long flap is released and permitted to extend back to its original position around the cuff. Once correctly positioned, the short flap is then released to wrap about the exterior of the long flap.

Figure 16:
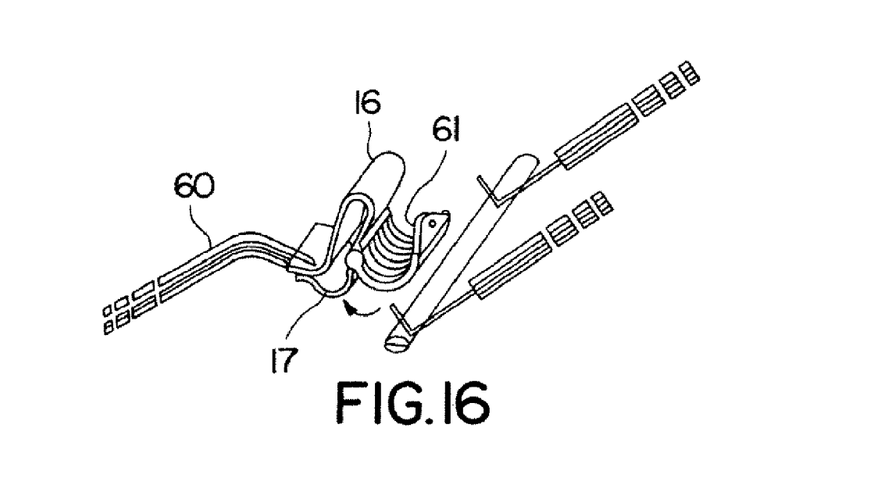

FIG. 16 shows an alternative method of presenting the tab electrodes to the nerve. In this method a single forceps 60 is used to hold the flaps 16, 17 and a suture 61 is strung through the semi-cylindrical cuff suture hole. The suture is then used to manipulate the cuff so that the tab electrodes are properly positioned about the nerve. Once the electrode portion is properly positioned, the nerve is released, the lead body and conductor are properly positioned and contacted to the stimulator and the incisions are closed, as well known.

Figure 17A:
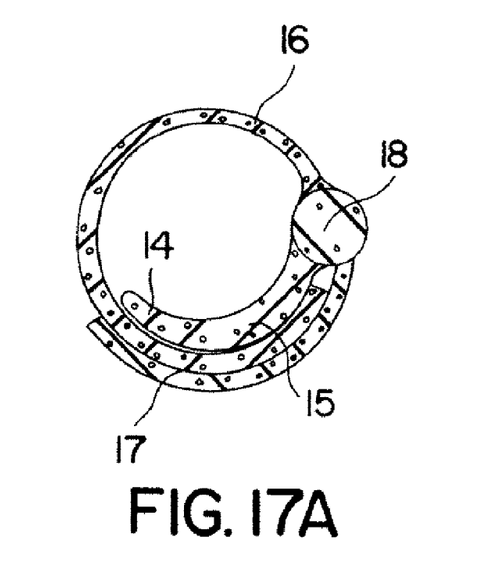
Figure 17B:
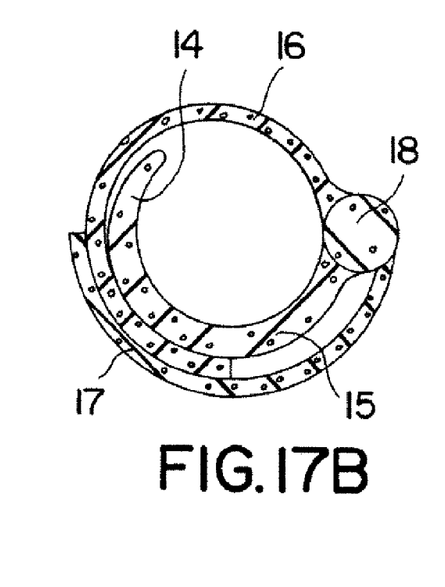
Figure 17C:
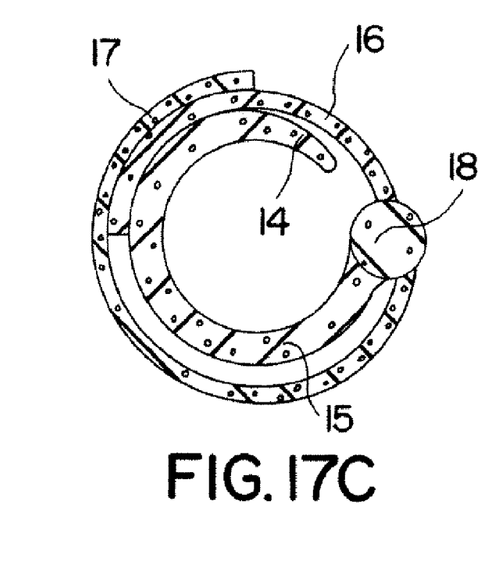

FIGS. 17 A, B and C disclose alternative embodiments of the electrode portion. FIG. 17A shows a semi-cylindrical cuff 15 having a long flap 16 which is substantially 360° in length, a short flap which is substantially 135° in radial length. The cuff 15 is approximately 90° in radial length. Suture hole portion 14 of cuff is shaded and it does not contribute to the actual radial length of cuff 15. FIG. 17B is a further alternative embodiment in which the cuff 15 has a radial length of 180°, the long flap 16 has a radial length of 270° and the short flap 17 has a radial length of 180°. FIG. 17C is a further alternative embodiment in which the cuff 15 has a radial length of 270°, the long flap 16 has a radial length of 180° and the short flap 17 has a radial length of 270°.

Figure 18A:
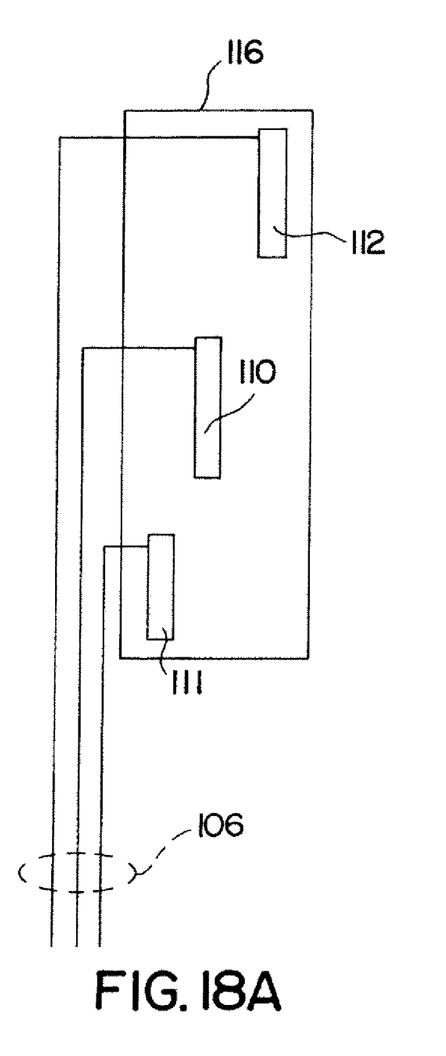
Figure 18B:
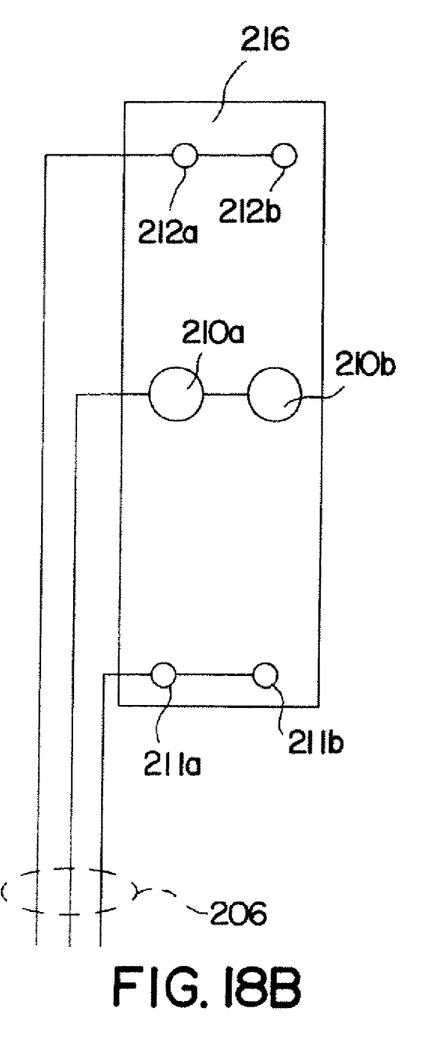

FIGS. 18A and B depict alternative embodiments of the electrodes used in the medical electrical lead of the present invention. FIG. 18A is a view of a semi-cylindrical cuff 116 shown as if it was flattened into one plane. Of course, cuff 116 is meant to be cylindrical in use and is illustrated only as a plane for purposes of clearly showing the electrode tab configuration. As seen, tabs are disposed longitudinally along cuff 116, the inner electrode tab 110 being electrically coupled to a first conductor and the outer two electrode tabs 111, 112 electrically coupled to a second conductor within a lead body 106. Turning now to FIG. 18B a further alternative embodiment is shown. As seen in this embodiment, inner electrode is composed of two or more electrode areas 210A and 210B. Outer electrode areas are comprised by two or more electrode areas 212A, 212B and 211A and 211B respectively. Areas 210 are coupled to a first conductor in the lead body 206 while areas 212 and 211 are coupled to a second conductor in the lead body. In this embodiment the surface area of the electrode areas 212 and 211 added together equal the total surface area of electrode 210. In each of the embodiments shown in FIG. 18B the electrodes may be formed from a bio-compatible metal, such as a platinum iridium alloy, but may also be formed from a conductive polymer.

Although the invention has been described in detail with particular reference to a preferred embodiment and alternate embodiments thereof, it will be understood variations and modifications can be effected within the scope of the following claims. Such modifications may include substituting elements or components which perform substantially the same function in substantially the same way to achieve substantially the same result for those described herein.

We claim:

1. A system for providing medical electrical stimulation, comprising:
    a first medical electrical lead comprising a first lead body and a first electrode portion, the first electrode portion being coupled to the first lead body, the first lead body comprising a first proximal section and a first distal section, the first distal section being thinner than the first proximal section;
    a second medical electrical lead comprising a second lead body and a second electrode portion, the second electrode portion being coupled to the second lead body, the second lead body comprising a second proximal section and a second distal section, the second distal section being thinner than the second proximal section;
    first and second suture sleeves positioned, respectively, on the first and second proximal sections; and
    a stabilizing block positioned on the distal sections of the first and second lead bodies, the stabilizing block having means for stabilizing the first and second electrode portions from moving out of position once they have been implanted.

2. The system of claim 1, wherein the means of stabilizing comprises a pliant polymer block having a series of slots, the slots dimensioned to frictionally engage with the first and second lead bodies.

3. The system of claim 1, wherein the first electrode portion comprises a root portion, a semi-cylindrical cuff extends from the root portion in a first radial direction, a long flap extends from the root portion in a second radial direction, the long flap extending over at least a portion of the semi-cylindrical cuff, and a short flap extends from the root portion in the first radial direction, the short flap extending over at least a portion of the long flap.

4. The system of claim 3, wherein the first radial direction ranges between 90 and 270 degrees.

5. The system of claim 4, wherein the second radial direction ranges between 180 and 360 degrees.

* * * * *